United States Patent [19]

Kates et al.

[11] Patent Number: 5,652,522
[45] Date of Patent: Jul. 29, 1997

[54] DIELECTRIC-LOADED SURFACE-CONDITION SENSOR AND METHOD

[75] Inventors: Ronald M. Kates, Newbury Park; Jennifer M. Butler, Pacific Palisades, both of Calif.

[73] Assignee: Hughes Electronics, Los Angeles, Calif.

[21] Appl. No.: 531,880

[22] Filed: Sep. 21, 1995

[51] Int. Cl.$^6$ .................................................. G01N 27/00
[52] U.S. Cl. ........................... 324/644; 324/642; 324/71.1
[58] Field of Search .................................. 324/637, 639, 324/642, 644, 647, 643, 71.1

[56] References Cited

U.S. PATENT DOCUMENTS

| | | | |
|---|---|---|---|
| 3,562,642 | 2/1971 | Hochschild | 324/644 |
| 4,052,666 | 10/1977 | Fletcher et al. | 324/644 |
| 4,511,842 | 4/1985 | Moran et al. | 324/338 |
| 5,105,157 | 4/1992 | Schmitt | 324/644 |
| 5,216,372 | 6/1993 | Zoughi et al. | 324/644 |
| 5,497,100 | 3/1996 | Reiser et al. | 324/643 |

*Primary Examiner*—Kenneth A. Wieder
*Assistant Examiner*—Glenn W. Brown
*Attorney, Agent, or Firm*—W. K. Denson-Low; V. D. Duraiswamy

[57] ABSTRACT

A dielectric-loaded, microwave sensor which can detect dielectric coatings, e.g., air, water and ice, on a road surface. The sensor includes an antenna having an aperture and also includes a dielectric member with a lower surface and an upper surface. The dielectric member is arranged with its lower surface across the antenna aperture and the sensor is embedded in a road with the dielectric member's upper surface coplanar with the road's surface. An antenna beam, which is incident upon the dielectric member, generates a return microwave signal which is the composite of microwave reflections from the dielectric member's inner and outer surfaces. Air, water and ice can be uniquely identified by the absence or presence of an amplitude minimum at predetermined frequencies of the return microwave signal. The thickness of an ice coating is determined by observation of the frequency of the amplitude minimum.

28 Claims, 5 Drawing Sheets

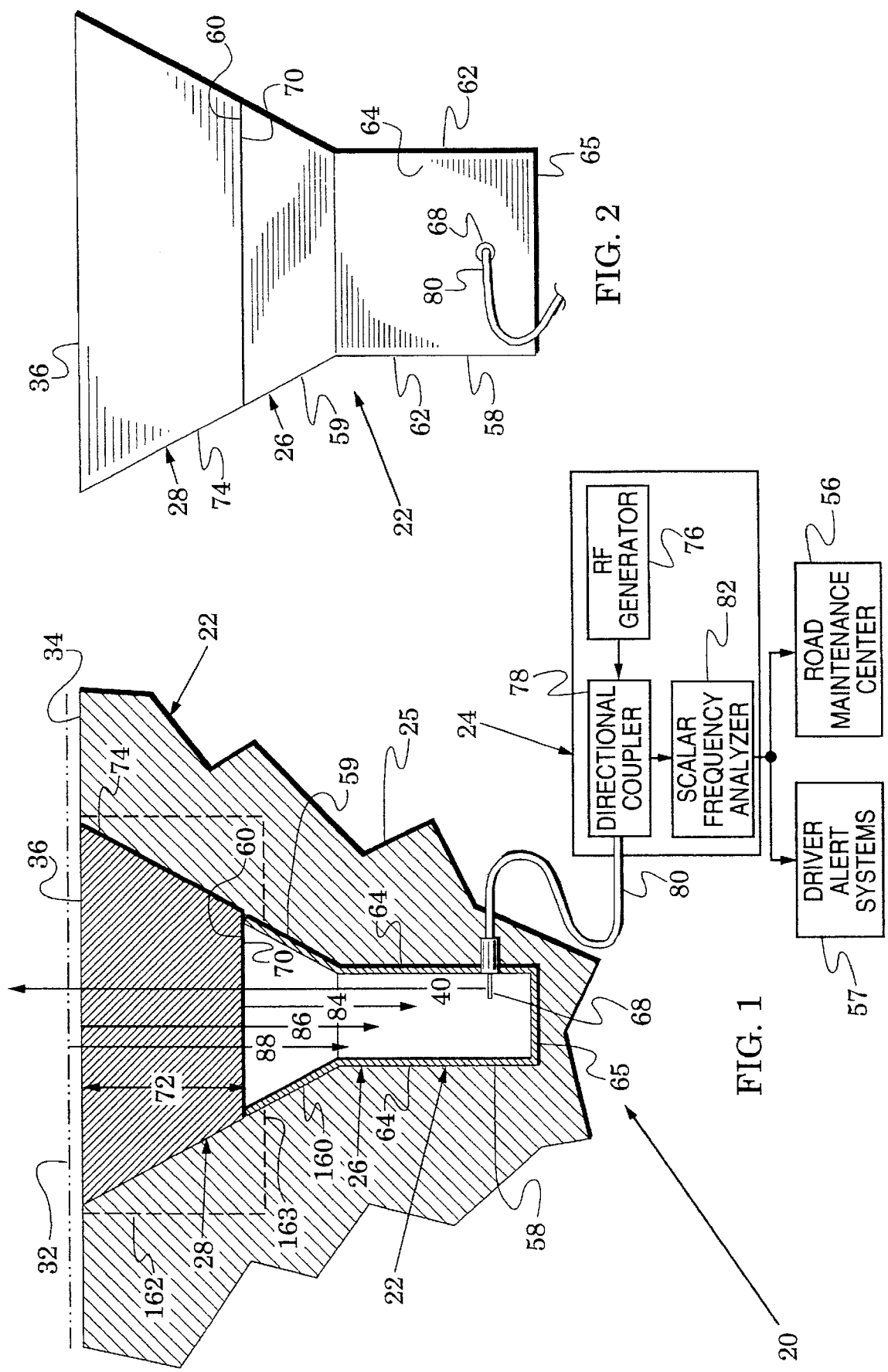

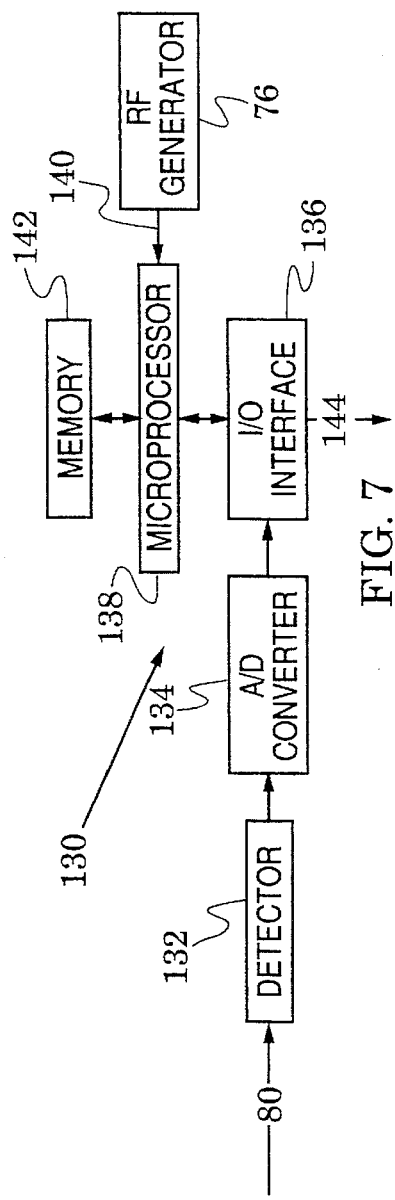
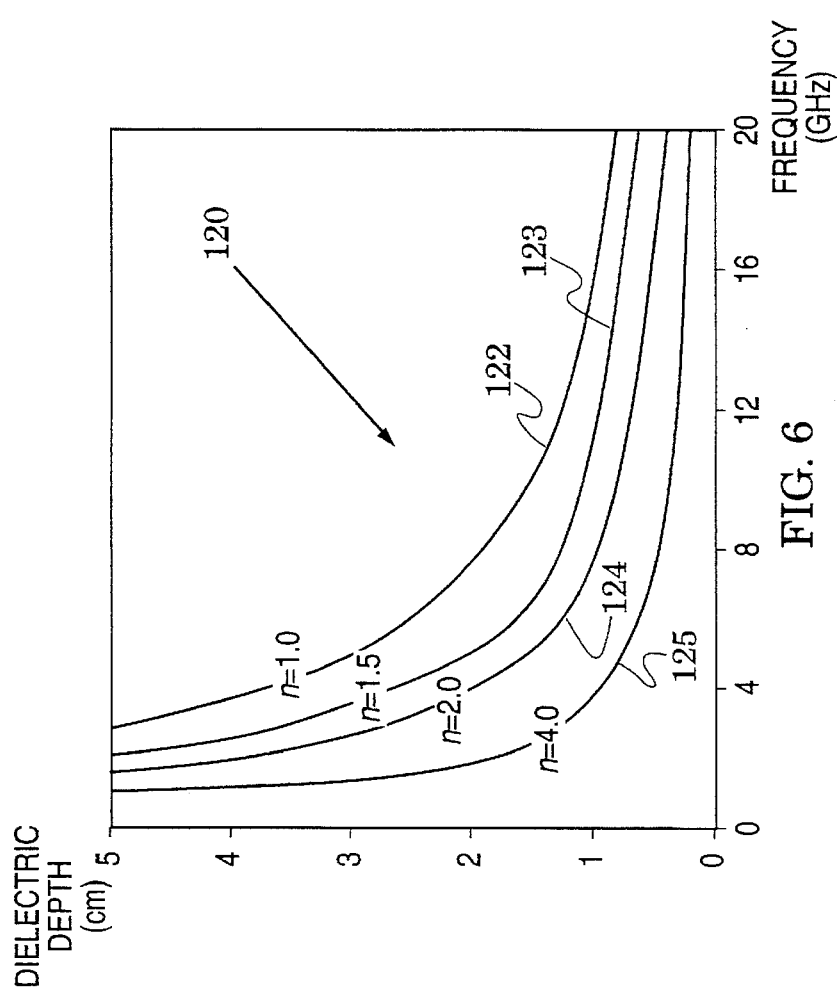
FIG. 6
FIG. 7

DIELECTRIC-LOADED SURFACE-CONDITION SENSOR AND METHOD

BACKGROUND OF THE INVENTION

1. Field of the Invention

The present invention relates generally to surface-condition sensors.

2. Description of the Related Art

The presence of water and ice on roads has been the primary cause of an enormous number of road accidents. Many of these accidents could have been prevented if these dangerous conditions were sensed and knowledge of them promptly communicated to approaching drivers. Accordingly, a successful road monitoring system would return significant rewards to the public in the form of injury and death prevention and economic savings.

Considerable efforts have been directed to the development of a practical road sensing system. For example, Intelligent Vehicle Highway System (IVHS) is a long term program funded in the United States at approximately 660 million dollars. This program includes the development of Advanced Traveler Information Systems (ATIS) which require sensors for monitoring of road conditions.

Road condition sensors must operate in the harsh environment of a road surface. Consequently, they preferably are simple, easily installed, resistant to the pressures and abrasions induced by vehicle fires, relatively unaffected by environmental effects (e.g., heat, cold, rain and ice) and reliable (e.g., having a low false-alarm rate).

A large number of systems have been proposed for detecting road surface conditions. One exemplary system positions a series of exposed electrodes on a road surface to measure electrical conductivity, ionic polarizability, stray capacitance and roadbed temperatures at different depths. These multiple measurements are integrated and analyzed to determine the presence of surface coatings, e.g., frost, ice, water and so on.

Another exemplary system positions a capacitance bridge in a sensor disk which is embedded in a road surface. Closely spaced conductors are also embedded in the surface for measurement of the resistance of road coatings and a thermistor is mounted below the road surface to detect whether the temperature is above or below freezing. The output of these sensors is combined and analyzed to determine the presence of different coatings on the road surface, e.g., the output of the capacitance bridge is used for detection of a water coating.

Although these systems may successfully sense road conditions, they require the installation of multiple components, would typically be sensitive to wear and abrasion, and involve the measurement and integration of several parameters.

Other ice-detection systems have proposed the use of microwave signals. In copending U.S. patent application Ser. No. 08/324,436 (filed Oct. 17, 1994 and assigned to Hughes Aircraft Company, the assignee of the present invention), now issued as U.S. Pat. No. 5,497,100, with issue date Mar. 5, 1996, assigned to Hughes Aircraft Company a microwave signal is directed at a road surface to generate a reflected signal. The reflected signal contains information which is indicative of dielectric coatings, e.g., water and ice, on the road surface. This system requires the generation of very high frequencies, e.g., millimeter waves, and is primarily intended for use on a moving vehicle.

SUMMARY OF THE INVENTION

The present invention is directed to a simple, inexpensive road-condition sensor and method which is reliable and resistant to long-term effects of the environment and vehicle-induced abrasion.

This goal is realized with the recognition that a composite reflection of a frequency-swept, microwave antenna beam from lower and upper surfaces of a dielectric member contains information which identifies a dielectric medium that is present upon the upper surface of the member.

It is recognized that the absence or presence of amplitude minima in the composite refection's amplitude response and the frequency location of these amplitude minima uniquely identifies the dielectric medium, e.g., air, water or ice. In addition, the frequency location of an ice-coat amplitude minimum corresponds to the thickness of the ice coating.

In particular, a coating of water on the dielectric member will be observed as an absence of an amplitude minimum, a coating of air will be observed as an amplitude minimum at a calibration frequency, and a coating of ice will be observed as an amplitude minimum at a frequency which is less than the calibration frequency. The coating thickness of the ice corresponds to the frequency delta between the detected frequency and the calibration frequency.

It is further recognized that the detection sensitivity is enhanced by reduction of other signal reflections which would otherwise tend to mask the reflections from the lower and upper surfaces of the dielectric member. Accordingly, the generation of the antenna beam should be accompanied by a close impedance match with free space impedance. In addition, the sensitivity for detection of ice is enhanced if the refractive index of the dielectric member is substantially equal to the refractive index of ice over the frequency range of the antenna beam.

These concepts are realized with a sensor that includes an antenna having an input port and an output aperture and a dielectric member which has a refractive index n in a predetermined microwave frequency range. The dielectric member is configured with an outer surface and an inner surface that is spaced from the outer surface by a dielectric thickness $t_{dm}$ that is substantially equal to $(mc)/(2nf_r)$ in which m is a predetermined integer, c is the speed of light and $f_r$ is a frequency in the predetermined frequency range. The dielectric member is arranged with its inner surface between the antenna and the member's outer surface and with its inner surface positioned across the antenna aperture.

In a system embodiment, the antenna is a waveguide horn which is embedded in a road with the upper surface of the dielectric member substantially coplanar with the road surface. A frequency-swept, microwave signal is inserted in the input port to excite the horn and generate an antenna beam which is incident upon the lower surface of the dielectric member. The composite return signal is coupled to a scalar spectrum analyzer through a directional coupler. To enhance sensitivity, the waveguide horn is configured with an aperture impedance which substantially matches free space impedance. To reduce reflections other than those from its lower and upper surfaces, the dielectric member is shaped to include the main lobe of the antenna beam within a peripheral wall of the member.

Because the upper surface of the dielectric member will be worn over time by abrasion of vehicle tires, the system is periodically calibrated by observing the frequency location of an amplitude minimum in the absence of water and ice on the upper surface. It is a feature of the present invention that wear of the upper surface affects only the calibration of the sensor system.

The novel features of the invention are set forth with particularity in the appended claims. The invention will be best understood from the following description when read in conjunction with the accompanying drawings.

BRIEF DESCRIPTION OF THE DRAWINGS

FIG. 1 is an illustration of a road sensor system, the illustration includes a sectional, side elevation view of a road-condition sensor installed in association with a road surface;

FIG. 2 is a front elevation view of the sensor of FIG. 1;

FIG. 6 is a diagram which relates the frequency difference between successive amplitude minima to the thicknesses of a dielectric member in the sensor of FIG. 1;

FIG. 7 is a block diagram of a scalar frequency analyzer in the system of FIG. 1.

DESCRIPTION OF THE PREFERRED EMBODIMENTS

Figure 4:
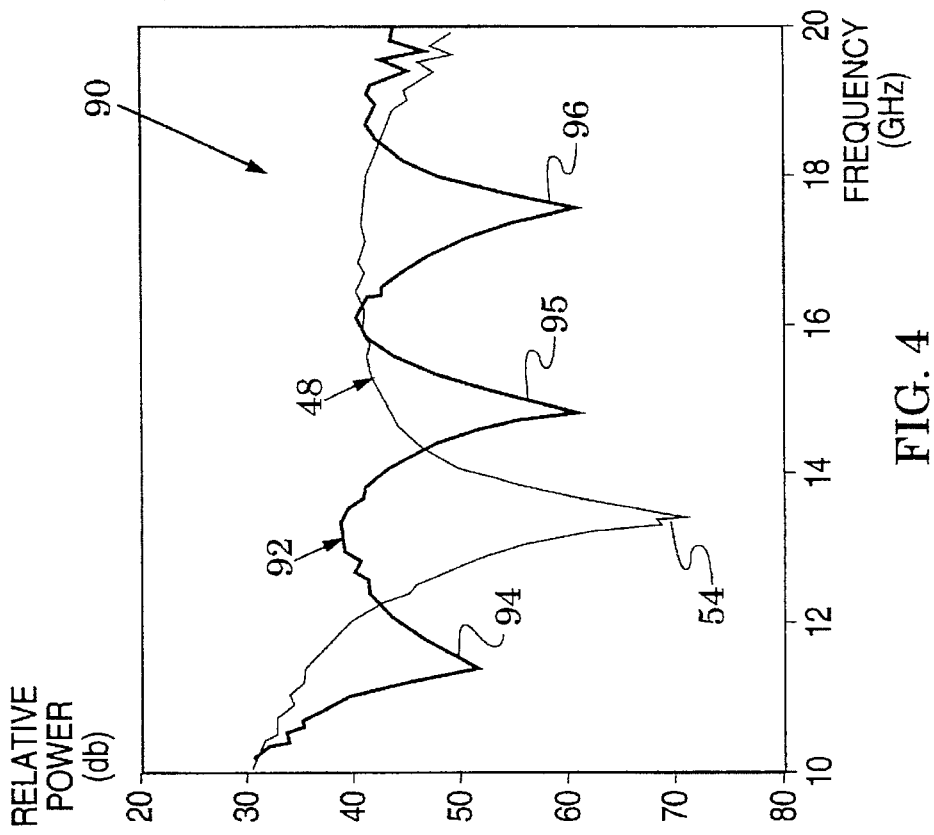
FIG. 4 is a diagram of amplitude responses from the sensor of FIG. 1 in response to a coating of ice on two different thicknesses of a dielectric member.

In FIG. 1, a surface-condition sensor system 20 is illustrated in association with a road 21. The system 20 includes a dielectric-loaded, surface-condition sensor 22 and a signal analyzer 24. The sensor 22 has an antenna in the form of a waveguide horn 26. It also has a dielectric member 28 and is embedded in the road 21 for the purpose of detecting the presence of a coating 32, e.g., air, water or ice, on the road surface 34. Accordingly, the sensor 20 is arranged to position an outer surface 36 of the dielectric member 28 substantially coplanar with the road surface 34. A frequency-swept microwave antenna beam 40 is directed at the dielectric member 28 from the horn 26 and a composite, return signal is reflected and received by the horn.

Figure 3:
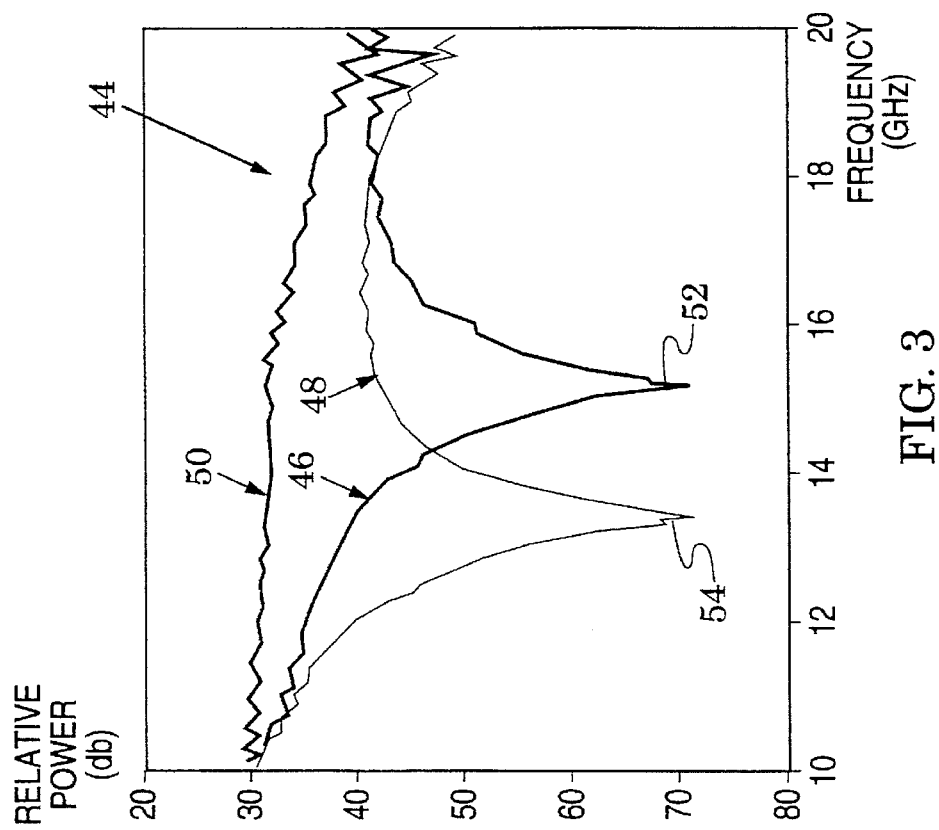
FIG. 3 is a diagram of amplitude responses from the sensor of FIG. 1 in response to coatings of air, water and ice on the road surface.

FIG. 3 is a graph 44 of amplitude responses 46, 48 and 50 of composite, return signals which result when the coating 32 is respectively air, ~1.5 millimeters of ice and water (for clarity of illustration, the response 48 is shown with a thinner line thickness than the responses 46 and 50). The amplitude response 46 has a minimum 52 at approximately 15.4 GHz and the amplitude response 48 has an amplitude minimum 54 at approximately 13.6 Ghz. In contrast, an amplitude minimum is missing in the amplitude response 50. A thicker coating of ice will cause the amplitude minimum 54 to move lower in frequency.

Thus, the composite, return signal from the sensor 22 contains information for identifying any one of air, water and ice on the upper member surface 32 (and, therefore, the road surface 32) and for determining the thickness of an ice coating. The signal analyzer 24 performs this identification and communicates the results to appropriate agencies. The agencies might include a road maintenance center 56 which could initiate warning signals and surface cleaning operations. The agencies might also include driver alert systems 57 which communicate an alarm to approaching vehicles.

In detail, the waveguide horn 26 has a waveguide throat 58 which is joined to an outwardly flaring section 59 which terminates in an antenna aperture 60. The throat 58 has a pair of narrow walls 62 and a pair of broad walls 64 which terminate in an end wall 65. An input port is mounted in the throat 58 for coupling to the electromagnetic field of the horn 26. In the sensor embodiment 22, the input port is a probe 68 which is positioned in one of the broad walls 64 so that it efficiently couples to the electric field of the horn 26 (e.g., the probe 68 is spaced $\lambda_{avg}/4$ from the end wall 65 in which $\lambda_{avg}$ is the average wavelength of the frequency-swept microwave signal 40).

The dielectric member 28 has an inner surface 70 which is spaced from its outer surface 36 by a thickness 72. The inner and outer surfaces 70 and 36 are connected by a circumferential wall 74. In the dielectric member 28, the circumferential wall 74 is shaped to continue the outward flare of the horn section 58.

The signal analyzer 24 includes an rf generator 76, e.g., a voltage-controlled oscillator, which is coupled to the probe 68 by a directional coupler 78 and a coaxial cable 80. Microwave return signals are coupled from the sensor 22 by the probe 68 and directed through the directional coupler 78 to a scalar spectrum analyzer 82.

In describing the operation of the sensor system 20, it is initially assumed that the refractive index $n_{dm}$ of the dielectric member 28 is substantially equal to the refractive index of ice over the frequency range of the frequency-swept microwave beam 40 (refractive index equals $(\epsilon_r')^{0.5}$ in which $\epsilon_r'$ is the real part of the complex dielectric constant $\epsilon_r^* = \epsilon_r' - j\epsilon_r''$). The beam 40 is excited in the horn 26 by a swept-frequency microwave signal which is coupled from the rf generator 76 to the probe 68 by the directional coupler 78. As the antenna beam 40 transits the aperture 60 it causes a first reflection signal 84 from the inner surface 70 and a second reflection signal 86 from the outer surface 36. The reflections 84 and 86 comprise a composite, return signal which is coupled to the scalar, spectrum analyzer 82 by the probe 68 and the directional coupler 78.

Although more exactly true in the antenna's far field, microwave theory teaches that the ratio of reflected intensity $I_r$ to incident intensity $I_i$ at the inner surface 70 is substantially $$\frac{I_r}{I_i} = \left( \frac{\eta_{dm} - \eta_{air}}{\eta_{air} + \eta_{dm}} \right)^2 \tag{1}$$

(in which $n_{air}$ is the refractive index of air) and the same ratio at the outer surface 36 is $$\frac{I_r}{I_i} = \left( \frac{\eta_{air} - \eta_{dm}}{\eta_{air} + \eta_{dm}} \right)^2. \tag{2}$$

Because the refractive index of the dielectric member 28 is greater than that of air, the reflected intensity at the inner surface 70 has a 180° phase shift from the incident beam 40. In contrast, the reflected intensity at the outer surface 36 has a 0° phase shift from the incident beam 40. Therefore, if the round trip from the lower surface 70 to the upper surface 36 and back to the lower surface 68 is an integral number m of wavelengths $\lambda_{dm}$ (in which $\lambda_{dm}$ is the microwave wavelength in the dielectric member 28), the reflection signals 84 and 86 will tend to cancel each other, i.e., generate an amplitude minimum. Because $\lambda_{dm}$ is equal to free space wavelength $\lambda$ divided by $n_{dm}$, there will be an amplitude minimum in the amplitude response of the composite, return signal (84 and 86 or 84 and 88) for all frequencies in which $$t_{td} = \frac{m\lambda}{2n_{dm}} \quad (3)$$

is true. In this equation, m is an integer (i.e., m=1, 2, 3 and so on) and $t_{td}$ is the total thickness of dielectric which has a refractive index substantially equal to the refractive index $n_{dm}$ of the dielectric member 28 (e.g., the dielectric member 28 or the sum of the dielectric member 28 and an ice coating 32).

The diagram 44 of FIG. 3 represents actual test data which was gathered with an acrylic dielectric member 28 in which $n_d$~1.65 and the thickness 70 (of FIG. 1) ~1.18 centimeters. When the coating next to the dielectric member was air, the amplitude minimum 52 was detected at ~15.4 GHz which is in accordance with equation (3) for m=2. For this test, equations (1) and (2) indicate that the intensity ratios at the inner surface 70 and the outer surface 36 were ~0.06. Therefore ~6% of the incident power was reflected from the inner surface 68 (the reflected signal 84 in FIG. 1) and ~5.6% (0.06(1−0.06)) of the incident power was reflected from the outer surface (the reflected signal 86 in FIG. 1). Because the intensity of the reflected signals only differ by ~0.3 db, their 180° phase difference causes the minimum 52 in the amplitude response 46 to be quite deep and, therefore, easily detected.

If an ice coating 32 (having the same refractive index of $n_{dm}$) is added to the upper surface 36 in FIG. 1, the reflected signal 86 is replaced by a reflected signal 88 from the top surface of the ice coating. In the actual test data of FIG. 3, the amplitude response 48 was detected after a 1.5 millimeter coating of ice was added to the upper surface 36 of the acrylic dielectric member. As shown, the minimum of the amplitude response shifted to the minimum 54 at approximately 13.6 GHz which is again in accordance with equation (3) because the thickness $t_{td}$ was then 1.18+0.15=1.33 centimeters. The intensity ratio at the upper ice surface is the same as the ratio at the lower surface 70, i.e., ~0.06. Therefore, the intensity of the reflected signals 84 and 88 only differ by ~0.3 db and their 180° phase difference generates a deep amplitude minimum 54.

In the test, the ice coating was then replaced with a coating of water which has a refractive index ~9 in this frequency range. With a water coating there will exist a reflected signal 86 from the bottom of the water coating and a reflected signal 88 from the top of the water coating. Equation (2) now yields ~0.48 as the intensity ratio for the reflected signal 86. In this case, ~6% of the incident power was reflected from the inner surface 68 and ~45% (0.48 (1−0.06)) of the incident power was reflected from the outer surface. These two reflected powers differ by ~8.8 db (10log (0.45/0.06)). Even when the reflected signals are 180° out of phase, the large reflected power (~45%) from the outer surface 36 is substantially unchanged by subtraction of the signal 84. This was confirmed by the lack of an amplitude minimum in the measured amplitude response 50.

Thus, air, ice and water coatings on the sensor 22 of FIGS. 1 and 2 cause the distinctly different amplitude responses 46, 48 and 50 of FIG. 3. The thickness of the ice coating is indicated by the frequency shift from a no-ice condition. For example, if the thickness of the ice had been doubled from 1.5 millimeter to 3.0 millimeters, equation (3) indicates that the minimum 54 of FIG. 3 would have moved from ~13.6 GHz to ~12.3 GHz.

If the refractive index $n_{dm}$ of the dielectric member 28 is significantly different from the refractive index of ice, an ice coating 32 in FIG. 1 will cause a reflection signal 86 to be reflected from the upper dielectric member surface 36 in addition to the reflected signal 88 from the top surface of the ice coating 32. If the refractive index $n_{dm}$ of the dielectric member 28 is greater than the refractive index of ice, this additional reflected signal 86 will lessen the depth of the minimum 54 in FIG. 3, i.e., the measurement sensitivity will be decreased.

If the refractive index $n_{dm}$ of the dielectric member 28 is less than the refractive index of ice, the additional reflected signal 86 will have a 0° phase shift (rather than the 180° phase shift of the signal 88 that is reflected from the upper surface of the ice coating). Consequently, the reflected signal 86 will cause minimums to occur at other frequencies. Unless the difference in refractive index is large, however, the depth of these minima will be much less than the minimum 54 in FIG. 3. Again, the measurement sensitivity will be decreased. For increased measurement sensitivity, the teachings of the invention are preferably practiced with dielectric members whose refractive index $n_{dm}$ is substantially equal to the refractive index of ice in the frequency range of the measurement.

Equation (3) above indicates the presence of multiple minima if the swept-frequency range is sufficiently large. This was verified in another test in which the thickness 70 of the dielectric member 28 was increased to ~2.87 centimeters and a coating of 15 millimeters of ice added to its upper surface. The graph 90 of FIG. 4 shows a measured frequency response 92 which has multiple minimums 94, 95 and 96 across a frequency range of 10–20 GHz. These minimums occurred for m=4, 5 and 6 in equation (3). For comparison, the amplitude response 48 of FIG. 3 is repeated in the graph 90.

Figure 5:
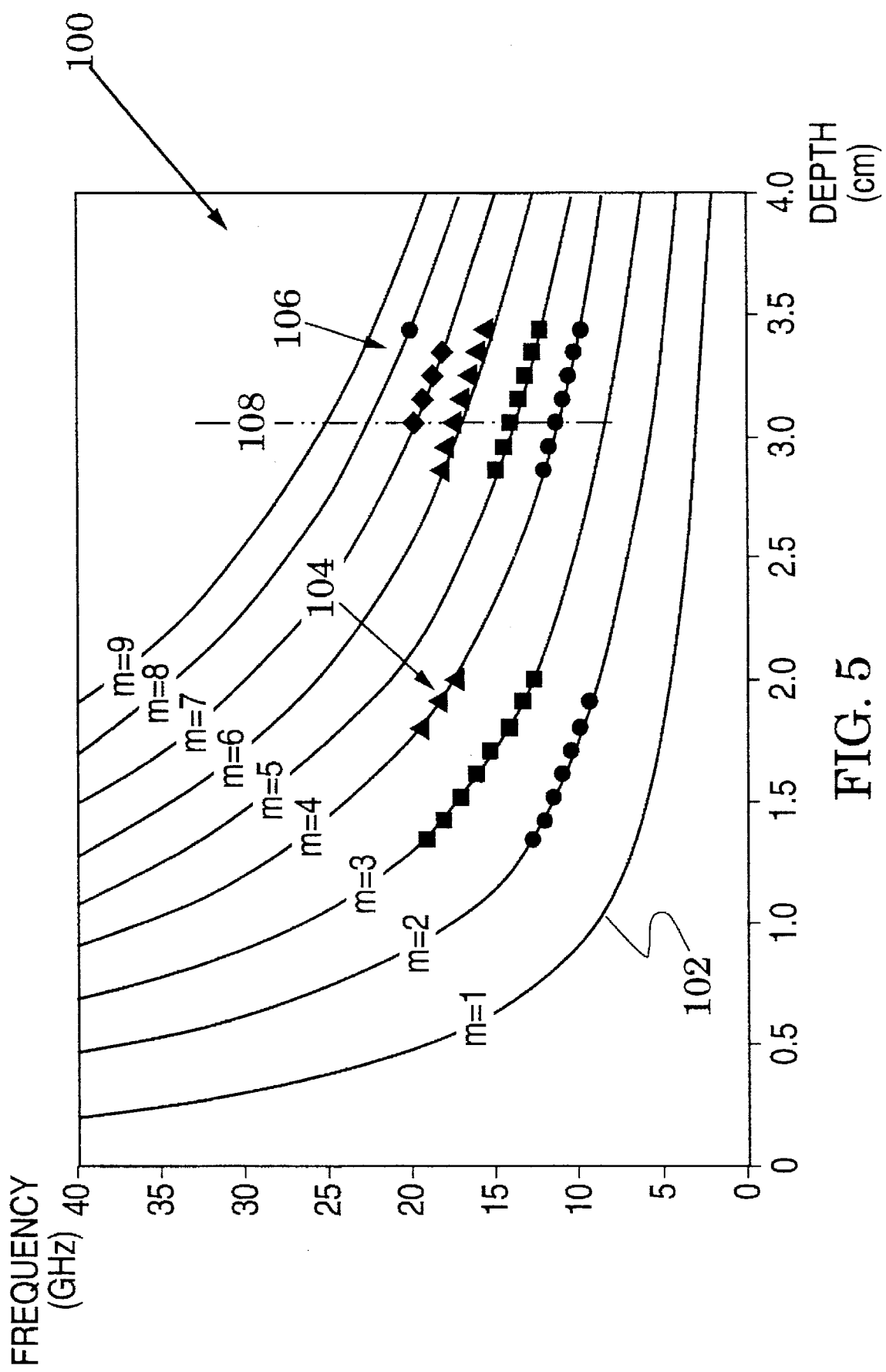
FIG. 5 is a diagram which relates the frequency of amplitude minima to different dielectric thicknesses in the sensor of FIG. 1, the diagram includes measured amplitude minima in a prototype of the sensor of FIG. 1.

In the graph 100 of FIG. 5, equation (3) is used to plot a curve 102 which illustrates the frequency of an amplitude minimum for various total thicknesses $t_{td}$ of dielectric in which m=1. The curve 102 is then repeated as m is varied from 2 to 9. These theoretical curves were experimentally verified in the previously mentioned tests. In a first experiment, a sensor having an acrylic dielectric member (28 in FIG. 1) with a thickness of 1.18 centimeters was placed in a temperature chamber. Amplitude minima were then measured as different thicknesses of ice were formed on the upper surface (36 in FIG. 1) of the dielectric member. The measured set 104 of amplitude minima are plotted in FIG. 5 as circles for the minimum in which m=2, as squares for the minimum in which m=3 and as triangles for the minimum in which m=3.

In a second experiment, the acrylic dielectric member was replaced by another having a thickness of 2.87 centimeters. Amplitude minima were again measured for different thicknesses of ice. The measured set 106 of amplitude minima are plotted in FIG. 5 as circles for the minimum in which m=4, as squares for the minimum in which m=5, as triangles for the minimum in which m=6, as diamonds for the minimum in which m=7 and as circles for the minimum in which m=8. For illustrative purposes, the broken line 108 is aligned with data points which were observed with a specific ice thickness. The refractive index of the acrylic test members varied from ~1.68 to ~1.8 over the frequency range of FIG. 5. The refractive index of ice is substantially 1.8 over this same range.

Equation (3) can be written as two equations with respective integers $m_1$ and $m_2$ in which $m_2=m_1+1$. If the relationship $m_2=m_1+1$ is substituted into the second equation, the second equation solved for $m_1$ and, finally, this relationship substituted into the first equation for $m_1$, an expression of $$t_d = \frac{c}{2n(f_2 - f_1)} \quad (4)$$

is derived for dielectric thickness $t_d$ as a function of the difference between minima in the amplitude response. This equation is plotted for different refractive indices in the graph 120 of FIG. 6. The different refractive indices of 1.0, 1.5, 2.0 and 4.0 are shown in FIG. 6 and they respectively yield the curves 122, 123, 124 and 125.

Equation (1) can be rewritten for two dielectric media with refractive indices n1 and n2 as $$n_2 = n_1 \left( \frac{1 + \sqrt{R}}{1 - \sqrt{R}} \right) \quad (5)$$

in which the intensity ratio $R = I_r/I_i$. Equation 5 and graph 120 of FIG. 6 illustrate that the teachings of the invention can be extended to the detection and measurement of dielectric media whose refractive index and thickness are both unknown. If such a dielectric medium is on the upper surface 36 of the sensor 22 in FIG. 1, the intensity of the composite reflected signal (of signals 84, 86 and 88) can be measured and the frequency separation of at least a pair of amplitude minima determined.

Equation 5 can then be used to find the unknown refractive index (the intensity of the signal 84 is known). With the refractive index known, data similar to that of the graph 120 can resolve the thickness of the previously unknown dielectric. These process steps can be used to identify the presence of an unknown dielectric, e.g., oil, that may be present along with the air, ice or water that the sensor 20 of FIG. 1 is primarily sensing.

In embodiments of the invention, the rf generator 76 of FIG. 1 can be realized as a voltage-controlled oscillator. The scalar spectrum analyzer 82 of FIG. 1 can be realized as any measurement apparatus which is capable of measuring the amplitude response (amplitude with respect to frequency) of the return signals, e.g., signals 84 and 86, which are coupled to the analyzer 82 by the directional coupler 78. For example, the analyzer 82 may be a commercially available scalar spectrum analyzer. In another embodiment, the analyzer could be realized as the analyzer 130 of FIG. 7. In this analyzer the return signals are coupled from the transmission line 80 (of FIG. 1) to a microwave detector 132. The output of the detector 132 is digitized in an analog-to-digital converter 134 and fed through an input/output interface 136 to a microprocessor 138. Frequency timing signals 140 are coupled to the microprocessor 138 from the rf generator 76. A memory 142 is used to store known refractive indices, known intensities of reflected signals (e.g., the signal 84), calibration frequencies, data from the curves of FIG. 6, predetermined amplitude responses and so on. Signals which indicate the identification of unknown dielectric media and their thicknesses are communicated on a signal line 144 from the I/O 136.

Figure 8:
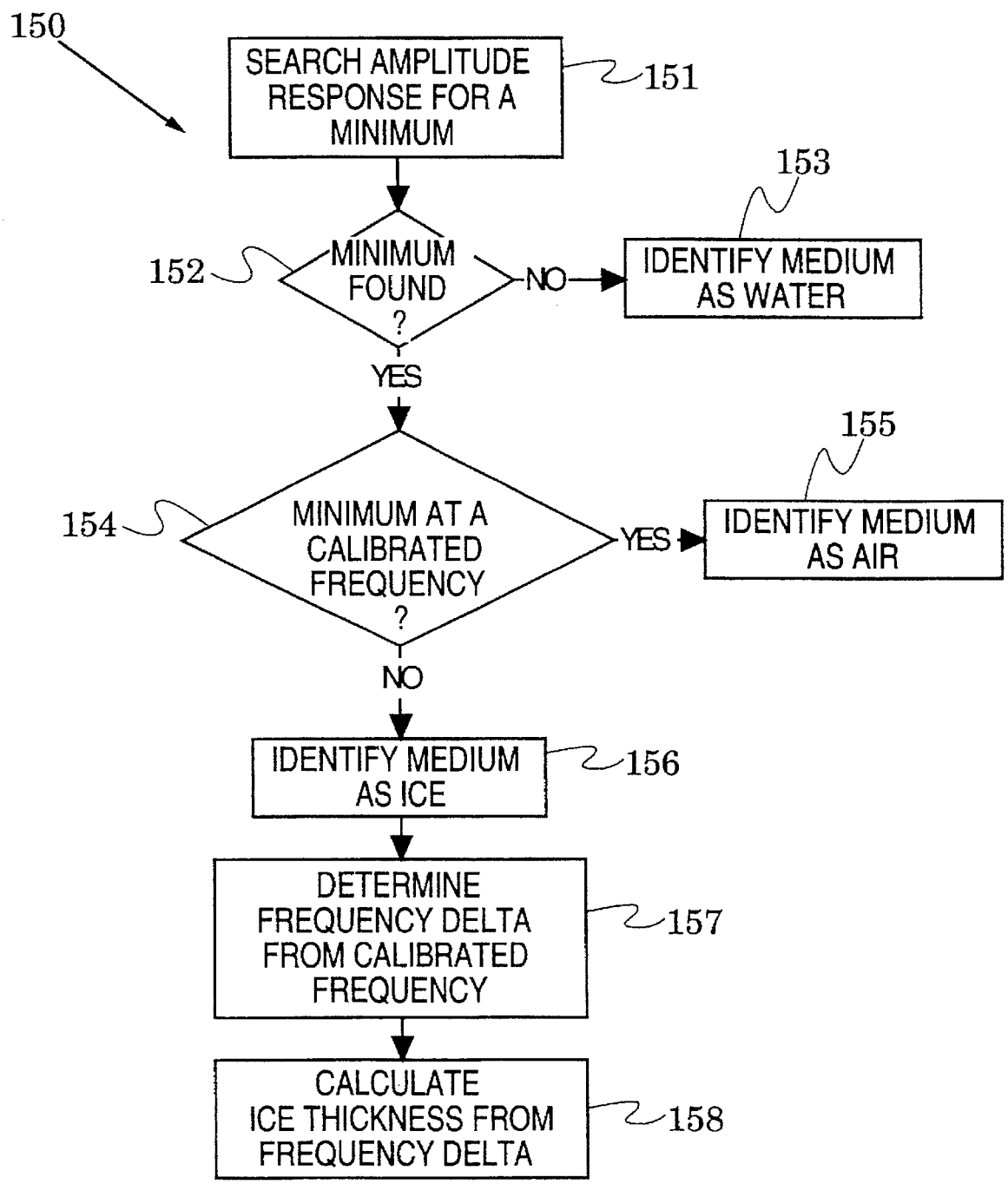
FIG. 8 is a flow chart of process steps in the scalar frequency analyzer of FIG. 7.

The microprocessor 138 can use a simple program to compare the return signals from the detector 132 with the frequency timing signals of the generator 76 and identify the dielectrics on the upper surface 36 of the sensor 22 in FIG. 1. For example, the flow chart 150 of FIG. 8 has a process step 151 in which a search is made for a minimum in the amplitude response (with reference to a predetermined threshold). If no minimum is found in decision 152, the program proceeds to process step 153 which identifies water on the surface 36. If a minimum is found at the calibrated frequency in decision 154, then process step 155 identifies the medium as air. If a minimum is found at a different frequency, process step 156 identifies the medium as ice. Process step 157 determines the delta frequency from the calibrated frequency and process step 158 calculates and communicates the thickness of the ice. For example, process step 157 may include accessing stored delta frequencies and ice thicknesses in the memory 142 of FIG. 7 and selecting the best fit with the observed delta frequency.

The sensitivity of the sensor system 20 of FIG. 1 is increased by configuring the waveguide horn 26 so that the impedance of its aperture 60 is closely matched to free space impedance (~377 ohms). This reduces reflections from the aperture which would otherwise tend to mask the reflections 84, 86 and 88. The horn 26 may be realized in various conventional horn shapes, e.g., pyramidal horns and E-plane sectoral horns. The shape of the flared section of these horns may be different from that shown in FIG. 1 in order to realize the desired aperture impedance. For example, the shape may be longer and with a shallower flare angle.

Obscuring reflections are also reduced by configuring the dielectric member 28 so that reflections from its peripheral wall 74 are reduced and/or directed away from the aperture 70. In general, the peripheral wall 70 is preferably spaced to at least include the main-lobe beamwidth of the antenna beam 40. This is accomplished in the sensor 20 of FIG. 1 by shaping the peripheral wall 74 to correspond with an imaginary continuation of the flared walls 160 of the horn's flared section 59 (the imaginary continuation is coincident with the wall 74 in FIG. 1). Alternatively, the peripheral wall could have the broken-line contour 162 which also includes the main-lobe beamwidth because it is outside the peripheral wall 74 (it surrounds the imaginary continuation of the flared walls 160). In addition, the contour 162 drops below the level of the aperture 70 to facilitate a lip 163 around the flared horn section 59 which could be used as an environmental seal.

When used to detect any one of air, water and ice, the dielectric member 28 is preferably made from a material whose refractive index substantially matches that of ice over a predetermined measurement frequency range. In addition, the material should have a high impact resistance and a superior abrasion resistance. Many polymers, e.g., acrylic plastics, can be used advantageously in embodiments of the invention.

When the sensor 22 of FIGS. 1 and 2 is installed in a road, the upper surface 36 of the dielectric member 28 is exposed to the wear of vehicular travel. In a feature of the present invention, however, wear of the upper surface 36 only affects the calibration of the sensor 22 and not, for example, its sensitivity and reliability. As the thickness 72 of the dielectric member 28 is reduced over time, the signal analyzer 24 periodically performs a calibration by sensing the response minimum 52 of FIG. 3. This calibration frequency becomes the frequency which indicates the presence of air on the upper surface of the sensor. Frequency of amplitude minimums at different frequencies (such as the minimum 54 in FIG. 3) are compared to the calibration frequency in determining ice thickness.

Abrasion marks on the upper surface 36 have little effect on the accuracy and sensitivity of the sensor 22 because they are quite small compared to the wavelength of a typical swept-frequency signal. For example, a swept signal from 12 to 16 GHz has wavelengths between 1.875 and 2.5 centimeters. Abrasion marks typically have much smaller spatial dimensions. This concept was experimentally verified by purposely abrading the upper surface 36 of a prototype sensor with a tool. This abrasion only caused a slight widening of the response minima 52 and 54 in FIG. 3.

The graph 100 in FIG. 5 illustrates that the frequency sensitivity of amplitude minima is increased by decreasing the thickness 70 of the dielectric member 28 in FIG. 1. That is, a given change in ice thickness will be represented by a greater change in the frequency of the amplitude minimum. In contrast, increasing the thickness 70 decreases the frequency range which is required to monitor a given range of ice thicknesses. In practice, the teachings of the graph 100 can be used to adapt the sensor 22 in accordance with design decisions. For example, an increased thickness of the dielectric member 28 will facilitate a reduction of the frequency range that is required of the rf generator 76 and this reduction would typically lower the cost of the generator.

The sensor 22 is simple, inexpensive and resistant to environmental effects. Vehicular tire wear only affects its calibration. The signal analyzer 24 can be realized with a relatively inexpensive voltage-controlled oscillator and a simple scalar frequency analyzer. The signal analyzer can be positioned at a convenient, central location. In practice, several of the detectors 22 could be installed in a road system, e.g., a freeway interchange, and a single signal analyzer 24 connected to them by transmission cables 80.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

We claim:

1. A sensor for use in identifying any one of air, water and ice and determining a thickness $t_i$ of said ice, comprising:

an antenna having an input port and an output aperture, said antenna configured to have an aperture impedance over a predetermined microwave frequency range; and a dielectric member having an outer surface and an inner surface that is spaced from said outer surface by a dielectric thickness $t_d$;

wherein:

said dielectric member has a refractive index n in a predetermined microwave frequency range;

said dielectric thickness $t_d$ is substantially equal to $(mc)/(2nf_r)$ in which m is a predetermined integer, c is the speed of light and $f_r$ is a frequency in said microwave frequency range; and said dielectric member is arranged with said inner surface between said antenna and said outer surface and with said inner surface positioned across said aperture;

said sensor returning a composite, microwave reflection signal in response to an input microwave signal that is swept over said frequency range and coupled to said input port, wherein said composite, microwave reflection signal includes reflections from said inner and outer surfaces and contains information for identifying said any one of air, water and ice on said outer surface and for determining said thickness $t_i$.

2. A sensor for use in identifying any one of air, water and ice and determining a thickness $t_i$ of said ice, comprising:

an antenna having an input port and an output aperture, said antenna configured to have an aperture impedance over a predetermined microwave frequency range; and a dielectric member having an outer surface and an inner surface that is spaced from said outer surface by a dielectric thickness $t_d$;

wherein:

said dielectric member has a refractive index n in a predetermined microwave frequency range;

said dielectric thickness $t_d$ is substantially equal to $(mc)/(2nf_r)$ in which m is a predetermined integer, c is the speed of light and $f_r$ is a frequency in said microwave frequency range; and said dielectric member is arranged with said inner surface between said antenna and said outer surface and with said inner surface positioned across said aperture;

said sensor returning a composite, microwave reflection signal in response to an input microwave signal that is swept over said frequency range and coupled to said input port, wherein said composite, microwave reflection signal includes reflections from said inner and outer surfaces and contains information for identifying said any one of air, water and ice on said outer surface and for determining said thickness $t_i$, wherein said refractive index n is substantially equal to the refractive index of ice in said predetermined microwave frequency range.

3. The sensor of claim 2, wherein said predetermined frequency band is contained within Ku band.

4. The sensor of claim 2, wherein:

said antenna is configured to radiate, in response to said input microwave signal, microwave energy from said aperture with a main-lobe beam width;

said dielectric member has a circumferential wall connecting said inner surface and said outer surface; and said dielectric member is shaped to include said beam width within said circumferential wall.

5. The sensor of claim 2, wherein said aperture impedance substantially matches free space impedance.

6. The sensor of claim 2, wherein said antenna comprises a waveguide horn.

7. The sensor of claim 6, wherein:

said waveguide horn has an outwardly-flaring section which adjoins said aperture;

said dielectric member has a circumferential wall connecting said inner surface and said outer surface; and said dielectric member is shaped to surround an imaginary extension of said outwardly-flaring section.

8. The sensor of claim 6, wherein said input port comprises a probe positioned in said waveguide horn to couple to the electric field of said waveguide horn.

9. The sensor of claim 6, wherein said waveguide horn is a pyramidal waveguide horn.

10. The sensor of claim 6, wherein said waveguide horn is an E-plane sectoral waveguide horn.

11. A sensor for use in identifying an unknown dielectric, comprising:

an antenna having an input port and an output aperture, said antenna configured to have an aperture impedance over a predetermined microwave frequency range; and a dielectric member having an outer surface and an inner surface that is spaced from said outer surface by a dielectric thickness $t_d$;

wherein:

said dielectric member has a refractive index n in a predetermined microwave frequency range;

said dielectric thickness $t_d$ is substantially equal to $(mc)/(2nf_r)$ in which m is a predetermined integer, c is the speed of light and $f_r$ is a frequency in said microwave frequency range; and said dielectric member is arranged with said inner surface between said antenna and said outer surface and with said inner surface positioned across said aperture;

said sensor returning a composite, microwave reflection signal in response to an input microwave signal that is swept over said frequency range and coupled to said input port wherein said composite, microwave reflection signal includes reflections from said outer and inner surfaces and contains information for identifying said unknown dielectric.

12. The sensor of claim 11, wherein:

said antenna is configured to radiate, in response to said input microwave signal, microwave energy from said aperture with a main-lobe beam width;

said antenna is configured to radiate microwave energy from said aperture with a main-lobe beam width;

said dielectric member has a circumferential wall connecting said inner surface and said outer surface; and said dielectric member is shaped to include said beam width within said circumferential wall.

13. A sensor system for identifying any one of air, water and ice and determining a thickness $t_i$ of said ice, comprising:

an antenna having an input port and an output aperture, said antenna configured to have an aperture impedance over a predetermined microwave frequency range;

a dielectric member having an outer surface and an inner surface that is spaced from said outer surface by a dielectric thickness $t_d$;

a swept-frequency microwave generator; and a microwave, scalar spectrum analyzer;

wherein:

said dielectric member has a refractive index n in a predetermined microwave frequency range;

said dielectric thickness $t_d$ is substantially equal to $(mc)/(2nf_r)$ in which m is a predetermined integer, c is the speed of light and $f_r$ is a frequency in said microwave frequency range;

said dielectric member is arranged with said inner surface between said antenna and said outer surface and with said inner surface positioned across said aperture;

said microwave generator is coupled to said input port for exciting said antenna and directing a swept-frequency antenna beam at said lower surface; and said scalar spectrum analyzer is coupled to said input port for receiving a composite, microwave reflection signal which includes reflections of said swept-frequency antenna beam from said inner surface and said outer surface, and for observing the absence or presence of amplitude minima at predetermined frequencies of said reflection signal which identifies said any one of air, water and ice on said outer surface and said thickness $t_i$.

14. The system of claim 13, wherein:

said antenna is configured to radiate microwave energy from said aperture with a main-lobe beam width;

said dielectric member has a circumferential wall connecting said inner surface and said outer surface; and said dielectric member is shaped to include said beam width within said circumferential wall.

15. The system of claim 13, wherein said aperture impedance substantially matches free space impedance.

16. The system of claim 13, wherein said signal analyzer includes a microwave detector coupled to said directional coupler for producing a detected amplitude response from said reflection signal.

17. The system of claim 13, wherein said scalar spectrum analyzer includes:

a microwave detector coupled to said directional coupler for producing a detected amplitude response from said reflection signal;

an analog-to-digital converter coupled to said microwave detector for converting said detected amplitude response to a digitized amplitude response;

a memory for storage of predetermined amplitude responses which are each representative of a different one of air, water and various thicknesses of ice; and a microprocessor programmed to compare said digitized amplitude response and said predetermined amplitude responses.

18. The system of claim 13, wherein said refractive index n is substantially equal to the refractive index of ice in said predetermined microwave frequency range.

19. The system of claim 13, wherein said predetermined frequency band is contained within Ku band.

20. The system of claim 13, wherein said antenna comprises a waveguide horn.

21. The system of claim 20, wherein said input port comprises a probe positioned in said waveguide horn to couple to the electric field of said waveguide horn.

22. A method for sensing the presence of any one of air, water and ice and determining a thickness $t_i$ of said ice, said method comprising the steps of:

providing a reference dielectric medium which has a refractive index n in a predetermined microwave frequency range, said reference dielectric medium also provided with an outer surface and an inner surface that is spaced from said outer surface by a reference thickness $t_r$;

exposing said outer surface to a coating of any unknown one of air, water and ice;

directing a frequency-swept antenna beam upon said inner surface to generate a return microwave signal which includes microwave reflections from said outer and inner surfaces;

identifying said unknown one of air, water or ice on said outer surface by observation of the absence or presence of an amplitude minimum at predetermined frequencies of said return microwave signal; and determining, in response to said identifying step, said ice thickness by observation of the frequency of said amplitude minimum.

23. A method for sensing the presence of any one of air, water and ice and determining a thickness $t_i$ of said ice, said method comprising the steps of;

providing a reference dielectric medium which has a refractive index n in a predetermined microwave frequency range, said reference dielectric medium also provided with an outer surface and an inner surface that is spaced from said outer surface by a reference thickness $t_r$;

exposing said outer surface to a coating of any unknown one of air, water and ice;

directing a frequency-swept antenna beam upon said inner surface to generate a return microwave signal which includes microwave reflections from said outer and inner surfaces;

identifying said unknown one of air, water or ice on said outer surface by observation of the absence or presence of an amplitude minimum at predetermined frequencies of said return microwave signal, and determining, in response to said identifying step, said ice thickness by observation of the frequency of said amplitude minimum, wherein said providing step includes the step of selecting said refractive index n to be substantially equal to the refractive index of ice in said microwave frequency range.

24. A method for sensing the presence of any one of air, water and ice and determining a thickness $t_i$ of said ice, said method comprising the steps of:

providing a reference dielectric medium which has a refractive index n in a predetermined microwave frequency range, said reference dielectric medium also provided with an outer surface and an inner surface that is spaced from said outer surface by a reference thickness $t_r$;

exposing said outer surface to a coating of any unknown one of air, water and ice;

directing a frequency-swept antenna beam upon said inner surface to generate a return microwave signal which includes microwave reflections from said outer and inner surfaces;

identifying said unknown one of air, water or ice on said outer surface by observation of the absence or presence of an amplitude minimum at predetermined frequencies of said return microwave signal, and determining, in response to said identifying step, said ice thickness by observation of the frequency of said amplitude minimum, and wherein said identifying step includes the steps of:
detecting said return microwave signal to produce a detected amplitude response; and
correlating said amplitude minimum in said detected amplitude response with frequencies of said frequency-swept antenna beam.

25. A method for sensing the presence of any one of air, water and ice and determining a thickness $t_i$ of said ice, said method comprising the steps of:

providing a reference dielectric medium which has a refractive index n in a predetermined microwave frequency range, said reference dielectric medium also provided with an outer surface and an inner surface that is spaced from said outer surface by a reference thickness $t_r$;

exposing said outer surface to a coating of any unknown one of air, water and ice;

directing a frequency-swept antenna beam upon said inner surface to generate a return microwave signal which includes microwave reflections from said outer and inner surfaces;

identifying said unknown one of air water or ice on said outer surface by observation of the absence or presence of an amplitude minimum at predetermined frequencies of said return microwave signal, and determining in response to said identifying step, said ice thickness by observation of the frequency of said amplitude minimum, and wherein said identifying step includes the steps of:
detecting said return microwave signal to produce a detected amplitude response;
comparing said detected amplitude response with a plurality of predetermined amplitude responses which are each representative of a different one of air, water and various thicknesses of ice; and
selecting one of said predetermined amplitude responses which best matches said detected amplitude response.

26. A method for sensing the presence of any one of air, water and ice and determining a thickness $t_i$ of said ice, said method comprising the steps of:

providing a reference dielectric medium which has a refractive index n in a predetermined microwave frequency range, said reference dielectric medium also provided with an outer surface and an inner surface that is spaced from said outer surface by a reference thickness $t_r$;

exposing said outer surface to a coating of any unknown one of air, water and ice;

directing a frequency-swept antenna beam upon said inner surface to generate a return microwave signal which includes microwave reflections from said outer and inner surfaces;

identifying said unknown one of air, water or ice on said outer surface by observation of the absence or presence of an amplitude minimum at predetermined frequencies of said return microwave signal, and determining, in response to said identifying step, said ice thickness by observation of the frequency of said amplitude minimum, and wherein said determining step includes the steps of:
measuring a frequency delta between an observed amplitude minimum and a calibrated amplitude minimum; and
establishing said ice thickness from said frequency delta.

27. A method for sensing the presence of any one of air, water and ice and determining a thickness $t_i$ of said ice, said method comprising the steps of:

providing a reference dielectric medium which has a refractive index n in a predetermined microwave frequency range, said reference electric medium also provided with an outer surface and an inner surface that is spaced from said outer surface by a reference thickness $t_r$;

exposing said outer surface to a coating of any unknown one of air, water and ice;

directing a frequency-swept antenna beam upon said inner surface to generate a return microwave signal which includes microwave reflections from said outer and inner surfaces;

identifying said unknown one of air, water or ice on said outer surface by observation of the absence or presence of an amplitude minimum at predetermined frequencies of said return microwave signal, and determining, in response to said identifying step, said ice thickness by observation of the frequency of said amplitude minimum, and wherein said identifying step includes the steps of:
responding to the absence of said amplitude minimum with the identification of water;
responding to the presence of an amplitude minimum at a frequency of substantially $(mc)/(2nt_r)$, in which m is a predetermined integer and c is the speed of light, with the identification of air; and
responding to the presence of an amplitude minimum at a frequency $f_i$ which is different from $(mc)/(2nt_{am})$ with the identification of ice;
and wherein said determining step includes the step of calculating said ice thickness $t_i$ as $t_i=\{(mc)/(2nf_i)\}-t_r$.

28. A method for sensing the refractive index and thickness $t_u$ of unknown dielectric, said method comprising the steps of:

providing a reference dielectric medium which has a reference refractive index $n_r$ in a predetermined microwave frequency range, said reference dielectric medium also having an outer surface and an inner surface that is spaced from said outer surface by a reference thickness $t_r$;

exposing said outer surface to a coating of said unknown dielectric;

directing a frequency-swept antenna beam upon said inner surface to generate a return microwave signal which includes microwave reflections from said outer and inner surfaces;

identifying the refractive index $n_u$ of said unknown dielectric by observation of the intensity of said return microwave signal;

detecting the frequency separation $\Delta_f$ between a pair of amplitude minima in said return microwave signal; and determining, in response to said detecting step, said thickness $t_u$ in accordance with the equation $t_u = c/(2n_u \Delta_f)$.

* * * * *